United States Patent
Want et al.

(10) Patent No.: US 6,250,482 B1
(45) Date of Patent: Jun. 26, 2001

(54) HOLDER FOR A FLUID RECOVERY SYSTEM

(75) Inventors: Nicholas Want, Manchester; Thomas S. Cochran, Antrim, both of NH (US); Jeff Harris, Wexford, PA (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 09/212,012

(22) Filed: Dec. 15, 1998

(51) Int. Cl.$^7$ ......................................................... A47F 5/14
(52) U.S. Cl. ..................................... 211/181.1; 211/133.4; 211/133.5; 5/503.1; 604/259; 604/322
(58) Field of Search ................... 604/259, 322; 211/181.1, 85.13, 133.4, 112, 133.5, 107, 106; 5/503.1; 248/153, 160, 302, 309.1, 311.2, 230.7, 230.1, 201, 218.4, 219.1

(56) References Cited

U.S. PATENT DOCUMENTS

| | | | |
|---|---|---|---|
| Re. 35,225 | 4/1996 | Herweck et al. | 604/321 |
| D. 328,790 | 8/1992 | Herweck et al. | D24/169 |
| D. 340,285 | 10/1993 | Herweck et al. | D24/169 |
| D. 393,387 * | 4/1998 | Gregor et al. | 248/302 |
| 3,363,626 | 1/1968 | Eidwell et al. | |
| 3,396,885 * | 8/1968 | Giondi . | |
| 3,559,939 * | 2/1971 | Luna | 248/305 X |
| 3,716,055 | 2/1973 | Schultze | 128/275 |
| 4,040,522 * | 8/1977 | Vickery . | |
| 4,146,138 * | 3/1979 | Davis | 211/106 X |
| 4,258,824 | 3/1981 | Kurtz et al. | 181/233 |
| 4,510,926 | 4/1985 | Inaba | 128/20 |
| 4,544,370 | 10/1985 | Elliott et al. | 604/319 |
| 4,550,749 | 11/1985 | Krikorian | 137/843 |
| 4,605,400 | 8/1986 | Kurtz et al. | 604/319 |
| 4,672,703 * | 6/1987 | Frazier | 5/503.1 |
| 4,715,856 | 12/1987 | Elliott et al. | 604/321 |
| 4,738,671 | 4/1988 | Elliott et al. | 604/319 |
| 4,747,844 | 5/1988 | Elliott | 604/319 |
| 4,807,567 * | 2/1989 | Atchley | 211/106 X |
| 4,826,032 | 5/1989 | Huyghe | 220/19 |
| 4,988,342 | 1/1991 | Herweck et al. | 604/321 |
| 5,039,046 * | 8/1991 | Brewster | 248/302 X |
| 5,114,416 | 5/1992 | Karwoski et al. | 604/321 |
| 5,141,504 | 8/1992 | Herweck et al. | 604/317 |
| 5,154,712 | 10/1992 | Herweck et al. | 604/321 |
| 5,286,262 | 2/1994 | Herweck et al. | 604/321 |
| 5,300,050 | 4/1994 | Everett et al. | 604/320 |
| 5,380,314 | 1/1995 | Herweck et al. | 604/403 |
| 5,397,299 | 3/1995 | Karwiski et al. | 604/4 |
| 5,401,262 | 3/1995 | Karwoski et al. | 604/321 |
| 5,425,068 | 6/1995 | Schaefer et al. | 378/197 |
| 5,507,734 | 4/1996 | Everett, Jr. et al. | 604/320 |
| 5,625,537 | 4/1997 | Neuder | 361/775 |
| 5,651,521 * | 7/1997 | Aberg | 248/218.4 |
| 5,722,964 | 3/1998 | Herweck et al. | 604/317 |
| 5,807,358 | 9/1998 | Herweck et al. | 604/320 |
| 5,865,408 | 2/1999 | Swisher et al. | 248/188.12 |
| 6,065,727 * | 5/2000 | Fitzgerald et al. | 248/302 |

FOREIGN PATENT DOCUMENTS

WO 98/30256  7/1998  (WO) .

* cited by examiner

*Primary Examiner*—Robert W. Gibson, Jr.
(74) *Attorney, Agent, or Firm*—Lahive & Cockfield, LLP

(57) ABSTRACT

A fluid recovery system holder having features of the present invention includes a housing for carrying the chest drain and a mounting assembly coupled to the housing for removably and replaceably mounting the housing on the support. The housing has an opening sized and shaped to receive the fluid recovery system. The housing can include a base member, a top member opposed to the base member, and a connecting assembly for connecting the base member and the top member. The top member has an opening sized and shaped to receive the fluid recovery system. The housing has a front face and an opposed back face. The connecting member is configured to allow visual inspection of the chest drain through the front face of the housing when the chest drain is positioned in the holder.

47 Claims, 12 Drawing Sheets

US 6,250,482 B1

HOLDER FOR A FLUID RECOVERY SYSTEM

BACKGROUND OF THE INVENTION

The present invention relates to fluid recovery systems for draining fluid from the body of a patient and, more particularly, to a holder for mounting such fluid recovery systems to a support.

Various fluid recovery systems have been developed to drain and collect fluids, such as blood from a body cavity. Such systems typically attach at least one tube to a body cavity of a patient for the removal of blood or other fluid following trauma or surgery. A one-way valve or fluid seal is provided in the system to prevent reflux of atmospheric air into the body cavity. The blood or other fluid is collected in a collection chamber provided within the fluid recovery system.

Medical professionals often recommend that patients attempt to leave their hospital beds and be mobile prior to removal of the fluid recovery system from the patient. As a result, unless a medical professional is available, the patient, who is often weak, must carry the fluid recovery system as the patient attempts to move. The patient may inadvertently drop or tip the chest drain. Perhaps, more importantly, the patient may not be physically strong enough to carry the fluid recovery system without assistance.

More generally speaking, in a hospital setting fluid recovery systems are occasionally bumped, jarred or even knocked-over. The destabilization of a fluid recovery system can present a number of problems which may adversely effect the operation of the system. For example, in the event the system is destabilized or knocked over, the one-way valve or fluid seal can be compromised by fluids within the system moving between the chambers of the fluid recovery system. Additionally, when collected fluid spills from the collection chamber to another chamber as a result of the system being destabilized, the volume of fluid removed from the patient must be recalculated to account for the volume of fluid spilled from the collection chamber. Furthermore, the siphon potential of the fluid recovery system can be diminished in the event of system destabilization.

In the case of fluid recovery systems such as thoracic cavity drains or chest drains, the chest drain preferably maintains a selected orientation relative to the patient, i.e., below the thoracic cavity or chest of the patient, in order to function best. Otherwise, fluid may not drain from the patient's body.

Therefore, there is a need for a holder for a fluid recovery system that facilitates the transport of the fluid recovery system by a patient or medical professional while concomitantly maintaining the fluid recovery system in a stable, upright, and operational position. There is also a need for a holder for mounting a fluid recovery system on a support, such as a mobile IV pole or a bedstand, that maintains the fluid recovery system in an operational position relative to the patient.

SUMMARY OF THE INVENTION

The present invention is directed to a holder for a fluid recovery system that facilitates the transport and support of the fluid recovery system while the system is attached to a patient. A fluid recovery system holder having features of the present invention includes a housing for carrying the chest drain and a mounting assembly coupled to the housing for removably and replaceably mounting the housing on the support. The housing has an opening sized and shaped to receive the fluid recovery system.

A fluid recovery system holder according to one embodiment of the invention, permits the fluid recovery system to be mounted on a support, such as a mobile IV pole or a bedstand. Mounting a fluid recovery system to a mobile IV pole provides mobility to the recovering patient without necessitating separation of the fluid recovery system from the patient. In addition, mounting a fluid recovery system, in particular a thoracic cavity drain, to a support inhibits destabilization of the thoracic cavity drain and can assist in ensuring that the thoracic cavity drain remains in the proper orientation relative to the patient. The holder, together with the support, can thus minimize jarring, tipping, or complete knock-over of the drain that can result in fluids spilling between the chambers of the drain, adversely effecting the operation of the drain.

The housing can include a base member, a top member opposed to the base member, and a connecting assembly for connecting the base member and the top member. The top member has an opening sized and shaped to receive the fluid recovery system. The housing has a front face and an opposed back face. The connecting member is configured to allow visual inspection of the chest drain through the front face of the housing when the chest drain is positioned in the holder.

The connecting member can include first and second U-shaped rods having an open portion and an opposed closed portion. Each rod is preferably oriented substantially perpendicularly to the top member and to the bottom member. The top member is connected to the U-shaped rods in selected proximity to the open portion of the U-shaped rods. The bottom member is connected to the U-shaped rods in selected proximity to the closed portion of the U-shaped rods.

According to one embodiment of the present invention, the mounting assembly can include a hook coupled to the housing. The hook preferably includes a proximal fastening element for fastening the hook to the housing, a generally C-shaped element coupled to the fastening element, and a spring-loaded distal element coupled to the C-shaped element. The C-shaped element is preferably configured to conform to a support having a generally circular cross-section with a preselected diameter. The distal element can be configured to extend and contract so as to allow the hook to receive the support. The mounting assembly can further include a hook securing element, such as a clasp for securing the hook to the support.

Alternatively, the mounting assembly can include first and second hooks coupled to the housing. In particular, the first and second hooks are coupled to the top member and to the bottom member, respectively. In addition, the first and second hooks are preferably positioned to open in opposite directions.

The holder can further include a handle coupled to the housing. The handle is preferably coupled to the housing in selected proximity to the top member and can be positioned at an angle to the front face of the housing so that the handle does not interfere with positioning the fluid recovery system in the holder.

An alternative embodiment of the invention provides a chest drain mount for mounting a chest drain on a support. The chest drain mount can include a first connecting element for connecting the mount to the chest drain, and a second connecting element for removably and replaceably connecting the mount to the support.

Yet another embodiment of the invention provides a chest drain assembly including a chest drain, and a holder for mounting the chest drain on a support. The holder can include a housing for carrying the chest drain, and a mounting assembly for removably and replaceably mounting the housing on the support. The housing preferably has an opening sized and shaped to receive the chest drain.

Still another embodiment of the invention provides a chest drain support assembly including a support, and a holder for mounting a chest drain on the support. The holder preferably includes a housing for carrying the chest drain, and a mounting assembly for removably and replaceably mounting the housing on the support. The housing has an opening sized and shaped to receive the chest drain. In a preferred embodiment the support is a stand, e.g., a mobile IV pole.

Yet another embodiment of the present invention provides a clamp for connecting a chest drain holder to a support. The clamp can include a fastening element coupled to the holder for fastening the clamp to the holder, and a support engaging member coupled to the fastening element and configured to conform to the support.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

DETAILED DESCRIPTION OF THE PREFERRED EMBODIMENTS

Embodiments of the present invention discussed herein provide a holder for a fluid recovery system, such as a thoracic cavity drain or chest drain, that facilitates the transport of the fluid recovery system and maintains the fluid recovery system in a stable and upright position during transport. The fluid recovery system holder additionally permits the fluid recovery system to be mounted on a support, such as a mobile IV pole or a bedstand.

As noted above, mounting a fluid recovery system to a mobile IV pole provides mobility to the recovering patient without necessitating separation of the fluid recovery system from the patient. In addition, mounting a fluid recovery system, in particular a thoracic cavity drain, to a support inhibits destabilization of the thoracic cavity drain and can assist in ensuring that the thoracic cavity drain remains in the proper orientation relative to the patient. The holder, together with the support, can thus minimize jarring, tipping, or complete knock-over of the drain that can result in fluids spilling between the chambers of the drain, adversely effecting the operation of the drain. A holder according to certain preferred embodiments of the present invention is rugged, light weight, and inexpensive to make. In addition, the holder is preferably easily sterilizable.

Figure 1:
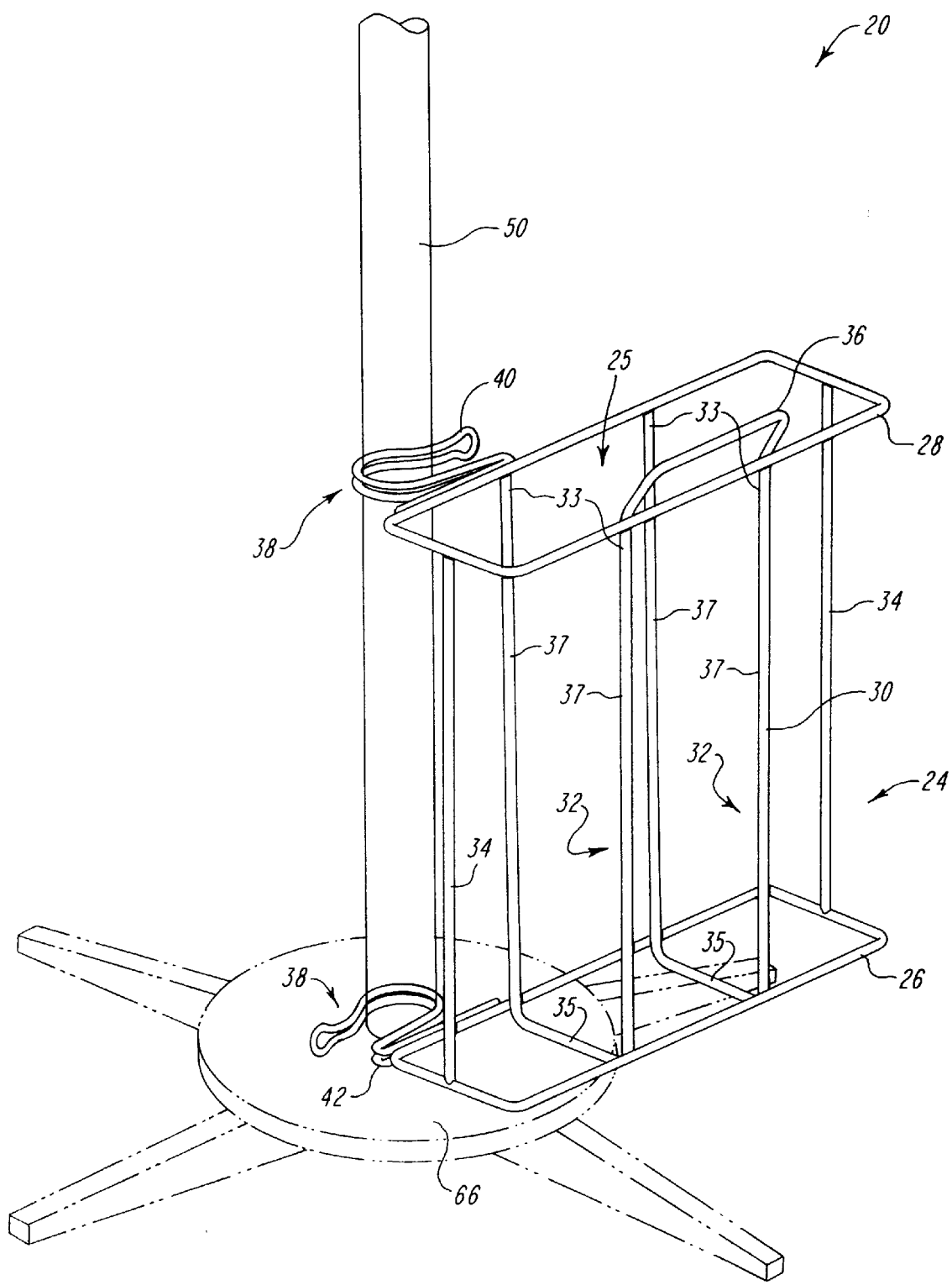
FIG. 1 is a perspective view of one embodiment of a holder for mounting a chest drain on a support according to the teachings of the present invention.
Figure 2:
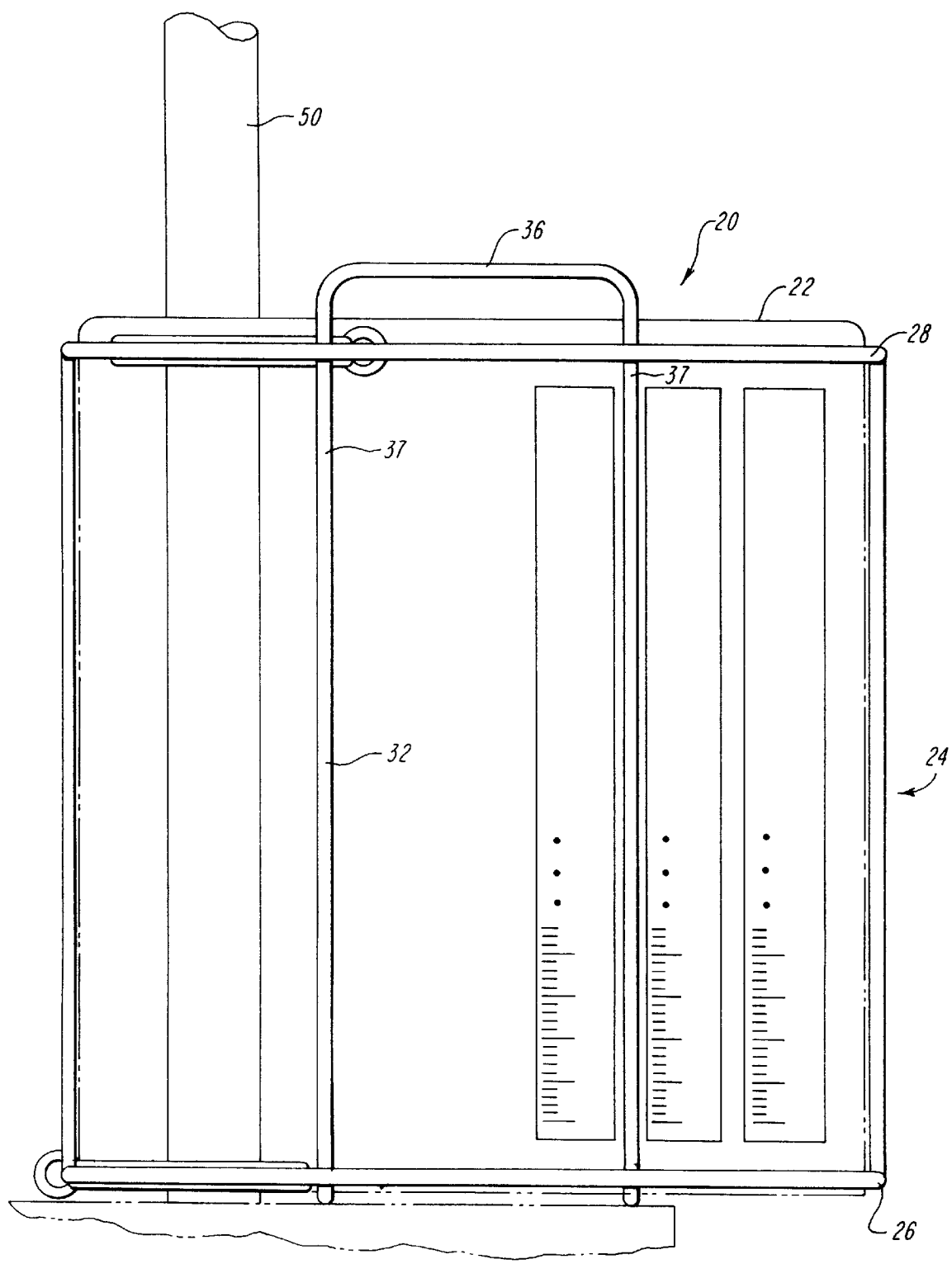
FIG. 2 is a front elevational view of the holder of FIG. 1, illustrating a chest drain positioned within the holder.

An exemplary fluid recovery system holder 20 for mounting a fluid recovery system 22 to a support 50 according to the teachings of the present invention is shown in FIGS. 1 and 2. The holder 20 includes a housing 24 for carrying the fluid recovery system 22, and mounting elements 38 coupled to the housing 24 for removably and replaceably mounting the housing 24 on the support 50. The housing 24 includes an opening 25 sized and shaped to receive the fluid recovery system 22.

In particular, the width and breadth of the opening 25 is preferably slightly larger, e.g., 1–4 centimeters larger, than the width and breadth of the widest and broadest portions of the chest drain 22. The opening 25 is preferably large enough to facilitate positioning of a chest drain 22 in the holder 20, and small enough to maintain the stability of the chest drain 22 once it is positioned in the holder 20. Those skilled in the art will appreciate that the opening 25 of the holder 20 can have a range of configurations between snugly fitting the chest drain to loosely fitting the chest drain.

In addition, the height of the holder 20 is at least two-thirds of the height of the chest drain 22, and is preferably greater than three-quarters of the height of the chest drain 22. When the height of the holder 20 approximates the height of the chest drain 22, the holder 20 is better able to stabilize the chest drain 22.

With reference to FIGS. 1, 2, 3, and 4, the fluid recovery system holder 20 of the present invention is particularly suited for mounting the fluid recovery system 22 to a support 50 and for manually transporting the fluid recovery system 22. The holder 20 is also well-suited for inhibiting the destabilization of fluid recovery systems used for draining fluid from the body of a patient. Such fluid recovery systems include thoracic cavity drains, also know as chest drains, for the collection of fluids, such as blood, from the thoracic cavity of a patient.

Figure 4:
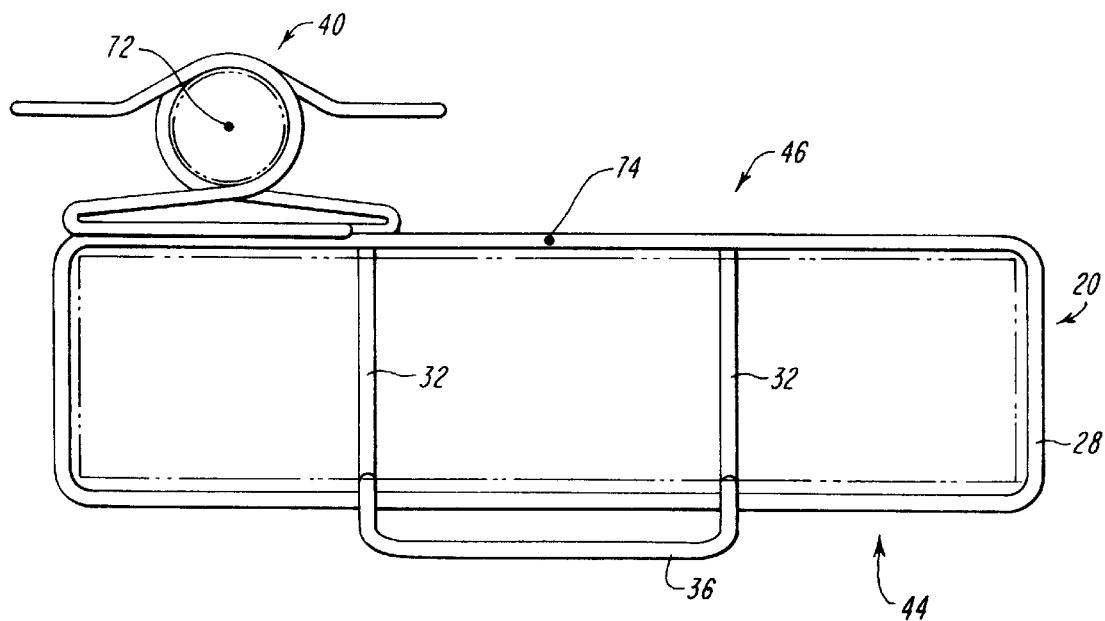
FIG. 4 is a top view of the holder of FIG. 1.

In a preferred embodiment the housing 24 includes a rectangular-shaped base member 26, a rectangular-shaped top member 28 opposed to the base member 26, and a connecting assembly 30 for connecting the base member 26 and the top member 28. The top member 28 forms the opening 25 for receiving the chest drain 22. The housing also includes a front face 44 and a parallel, opposed back face 46, as shown in FIG. 4.

In a preferred embodiment, the connecting assembly 30 includes first and second U-shaped rods 32 each of which includes an open portion 33 and an opposed closed portion 35 connected by a pair of legs 37. Each of the legs 37 is preferably oriented substantially perpendicularly to both the top member 28 and the bottom member 26. The top member 28 is connected to the U-shaped rods 32 in selected proximity to the open portion 33 of the U-shaped rods 32. The base member 26 is connected to the U-shaped rods 32 in selected proximity to the closed portion 35 of the U-shaped rods 32. The closed portions 35 of the U-shaped rods 32 extend across the base member 26 to provide support for the chest drain 22 when inserted in the housing 24.

Alternatively, the connecting assembly can include a single U-shaped rod with the top member connected to the open portion and the bottom member connected to the closed portion. The connecting assembly 30 also includes two end rods 34 that extend between the top member 28 and the base member 26 at opposing sides of the housing 24 to provide lateral support to the chest drain 22.

The connecting assembly 30 is preferably configured to allow visual inspection of the chest drain 22 through the front face 44 of the housing 24 when the chest drain 22 is positioned in the holder 20, as illustrated in FIG. 2. In particular, it is preferable for the legs 37 of the connecting assembly 30 to be positioned such that the volume of fluid within the chambers of the chest drain 22, particularly the collection chamber, can be measured without necessitating removal of the chest drain 22 from the housing 24.

The housing 24 is preferably constructed from materials suitable for use in a sterilized environment, including, for example, medical grade stainless steel. Stainless steel is well-suited because it is relatively inexpensive and strong, and is easily sterilized through autoclaving. In a preferred embodiment the holder is made of thin, e.g., approximately 0.3 to 1.0 cm diameter, stainless steel rods. However, the housing 24 can also be made of other suitable materials such as, for example, plastic. The material used for the housing preferably does not easily deform or break. The portion of the housing 24 that contacts the fluid recovery system 22 is preferably smooth so as to facilitate easy insertion and withdrawal of the system and so that the housing 24 does not damage the system 22.

In a preferred manufacturing process for the housing 24, the top member 28, the bottom member 26, and the components of the connecting assembly 30, i.e., the first and second U-shaped members 32 and the end rods 34, are constructed individually from stainless steel wire. The U-shaped members 32 and the end rods 34 are then welded to the top member 28 and the bottom member 26 to complete assembly of the housing 24. Any extra weld is next ground off and the joints between the welded components of the housing 24 are polished. Finally, the complete housing 24 is preferably electro-polished. Those skilled in the art will appreciate that other approaches to connecting the components of the housing may be used in practicing the invention.

Figure 5:
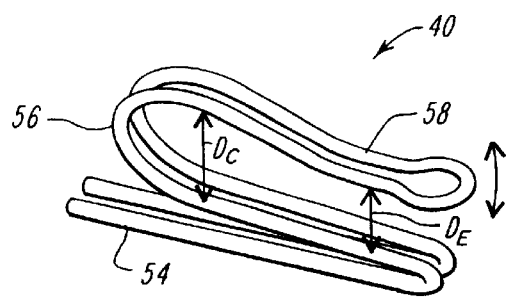
FIG. 5 is a perspective view of one embodiment of a mounting element for use with the holder of FIG. 1.

The mounting assembly 38 can include at least one hook 40 coupled to the housing 24. As shown in FIG. 5, the hook 40 includes a proximal fastening element 54 for fastening the hook 40 to the housing 24, a generally C-shaped element 56 coupled to the fastening element 54, and a spring-loaded distal element 58 coupled to the C-shaped element 56.

The C-shaped element 56 is configured to conform to the support 50. The distal element 58 is configured to extend and contract so as to allow the hook 40 to receive the support 50. In particular the diameter of the C-shaped element 56, indicated by line Dc in FIG. 5, is preferably greater than or equal to the diameter of the support 50. The distance between the distal end 58 and the proximal fastening element 54, indicated by line DE in FIG. 5, is preferably less than the diameter of the support 50.

Those skilled in the art will appreciate that the mounting assembly can have elements other than a generally C-shaped element. For example, the mounting assembly can have generally square or triangular shaped elements. The generally square or triangular shaped elements can have an open portion for receiving a support laterally. Alternatively, the mounting assembly can be configured for mounting over the top of a pole, e.g., the mounting assembly can include at least one ring for sliding over the top of an IV pole. In addition, the mounting assembly can be configured to accommodate a variety of support shapes, sizes and cross-sectional diameters.

Figure 7C:
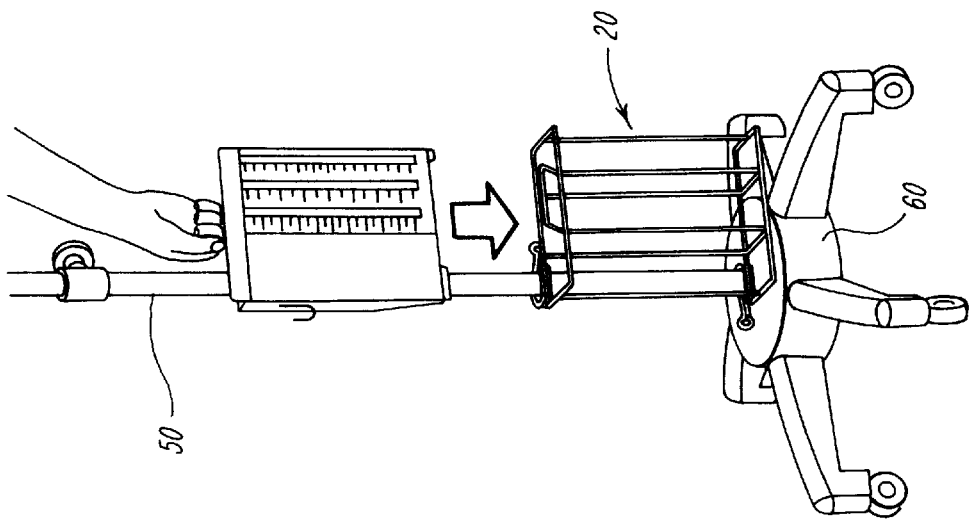
FIGS. 7A–7C are perspective views of three stages in the mounting of the holder of FIG. 1.
Figure 7B:
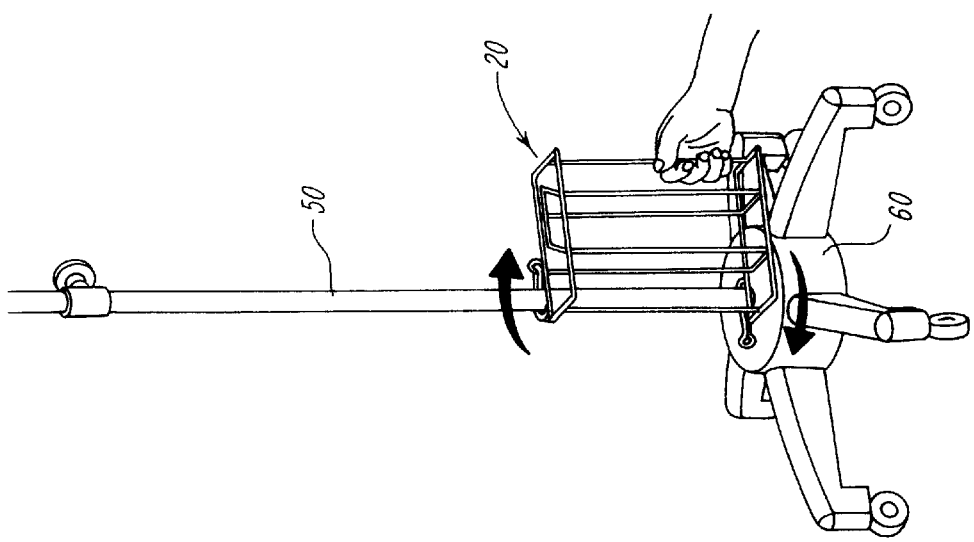
Figure 7A:
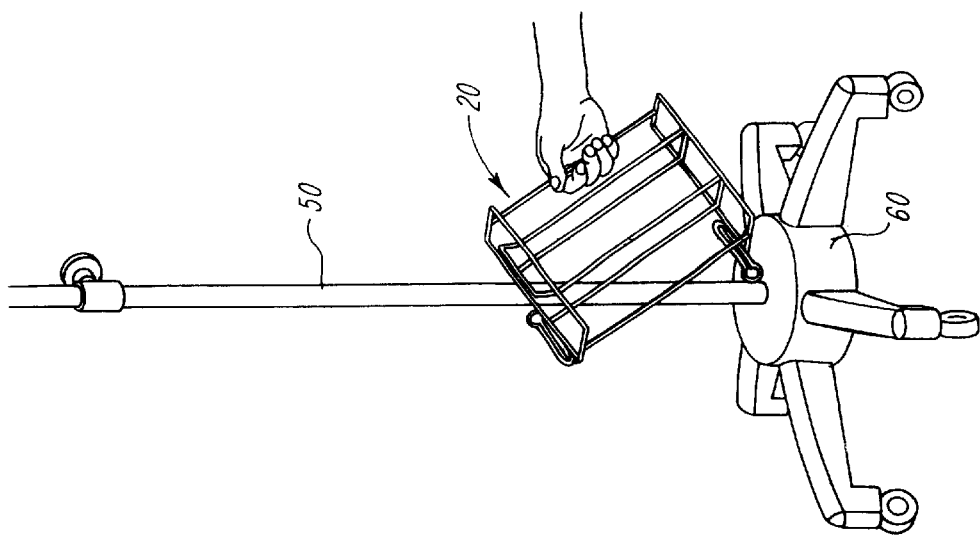
Figure 11:
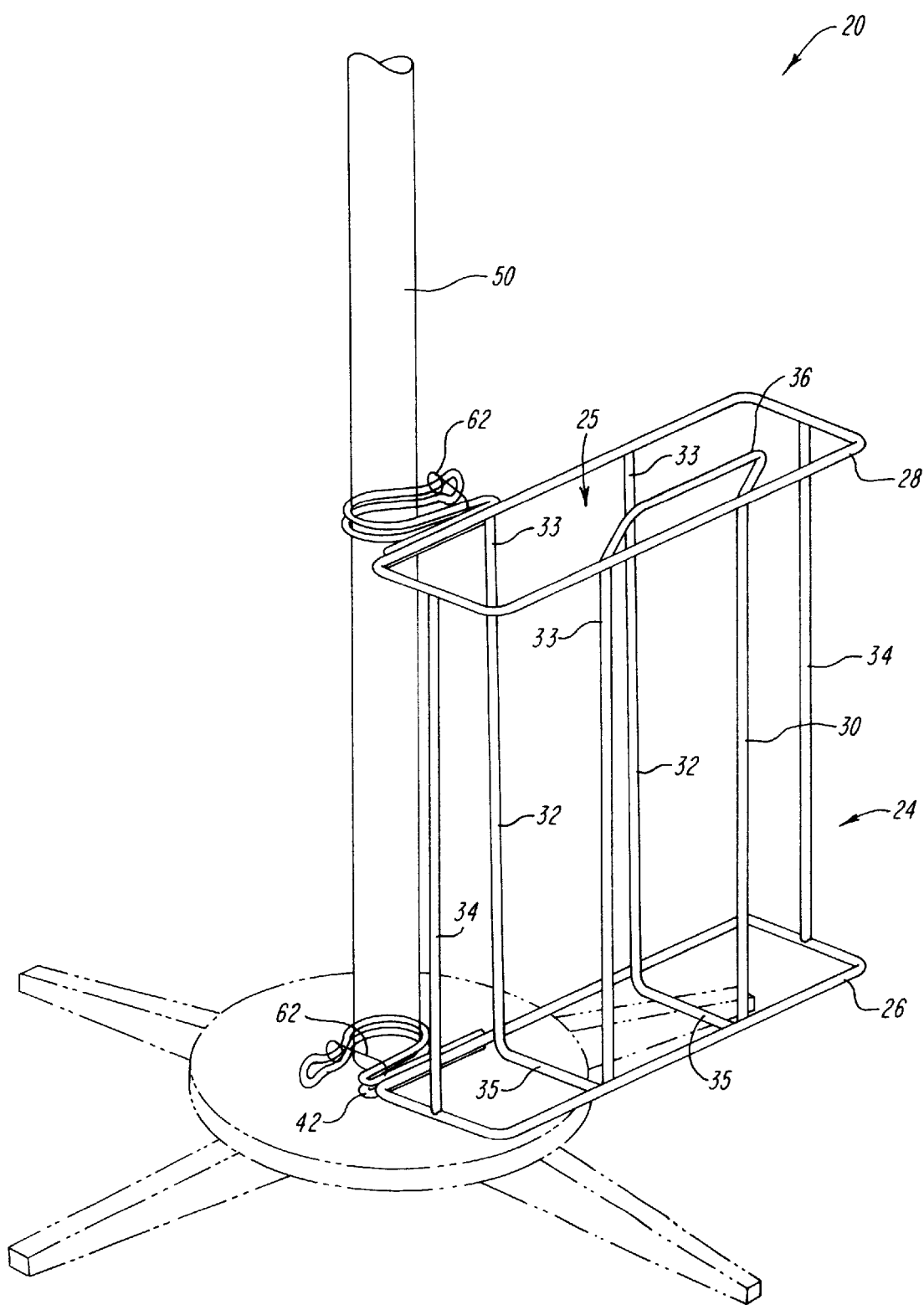
FIG. 11 is a perspective view of the holder of FIG. 1, illustrating the clasp for securing the holder to the support.

When a user inserts a support 50 into the hook 40 the distal element 58 deflects away from the fastening element 54 to allow the support to pass into the C-shaped element 56. Once the support 50 has passed into the hook 40, the distal end resiliently returns to its initial position. With reference to FIG. 11, the mounting assembly 38 can further include a hook securing element, such as a clasp 62 for securing the hook 40 to the support 50. In a preferred embodiment, the support is a mobile stand 50, e.g., a mobile IV pole, as shown in FIGS. 7A–7C. Alternatively, the support can be a non-mobile stand 50, as shown in FIG. 1.

Again with reference to FIG. 1, according to a preferred embodiment, the mounting assembly includes first and second hooks 40, 42 coupled to the housing 24. In particular, the first and second hooks 40, 42 are coupled to the top member 28 and to the bottom member 26, respectively. In addition, the first and second hooks 40, 42 are positioned to open in opposite directions. Those skilled in the art will appreciate that mounting mechanisms other than the mounting hooks 40 and 41 may be used to practice the present invention. For example, clamps, Velcro strips, and straps may all be used to mount the holder.

Figure 9:
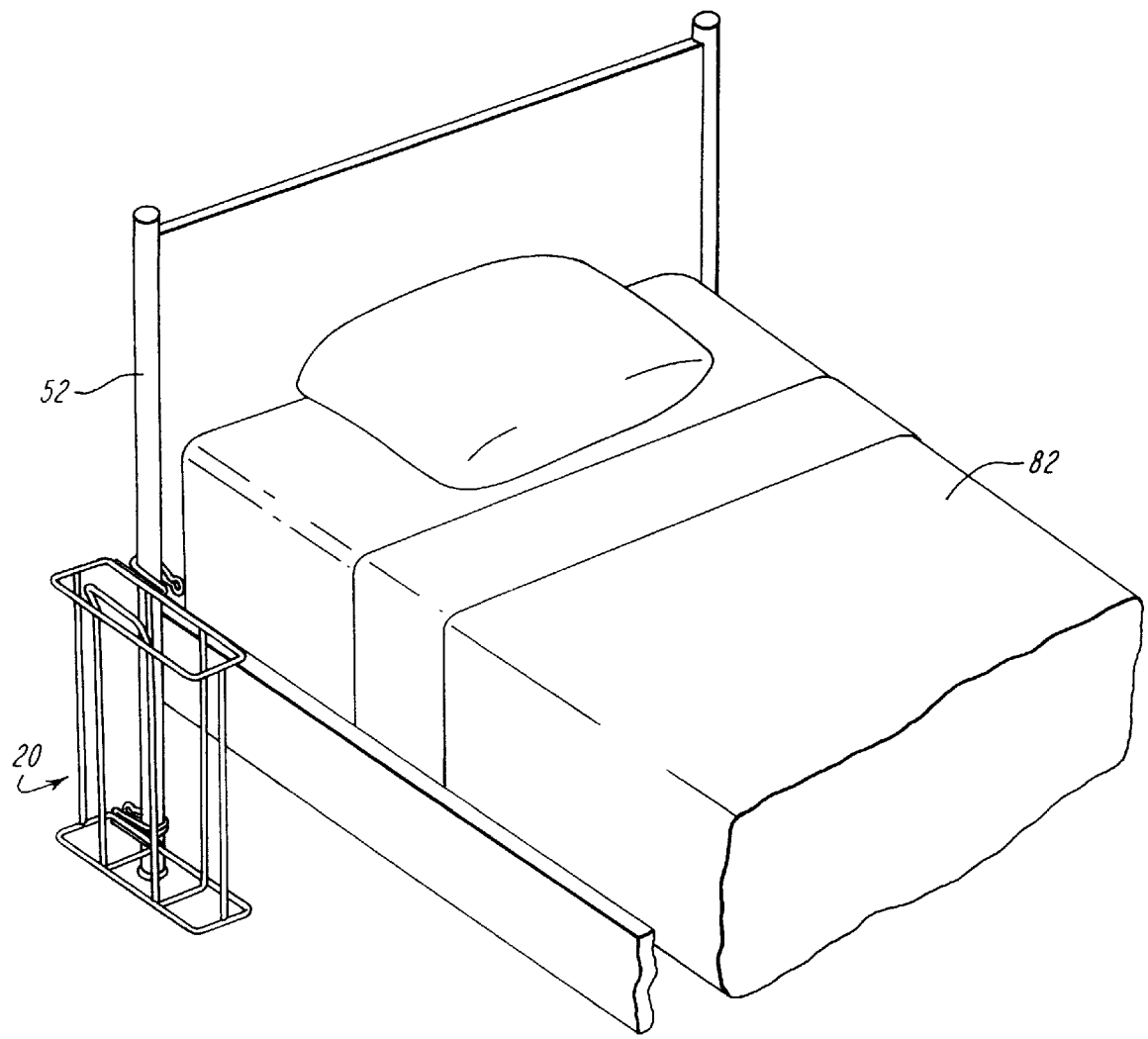
FIG. 9 is a perspective view of the holder of FIG. 1 mounted on a bedpost.

In addition, with reference to FIGS. 1 and 4, an alternative embodiment of the present invention can provide hooks 40, 42 in a vertical plane perpendicular to the back face 46 of the holder 20 and coupled in proximity to the top of the back face 46 of the holder 20. This configuration of the hooks allows one to mount the holder 20 on a horizontal structure, such a headboard of a bed. With reference to FIGS. 1 and 9, a user can mount the embodiment of the holder 20 shown in FIG. 1, on a bedpost 52 preferably at a location below the height of the top surface 82 of the mattresses to facilitate the operation of the fluid recovery system.

Figure 3:
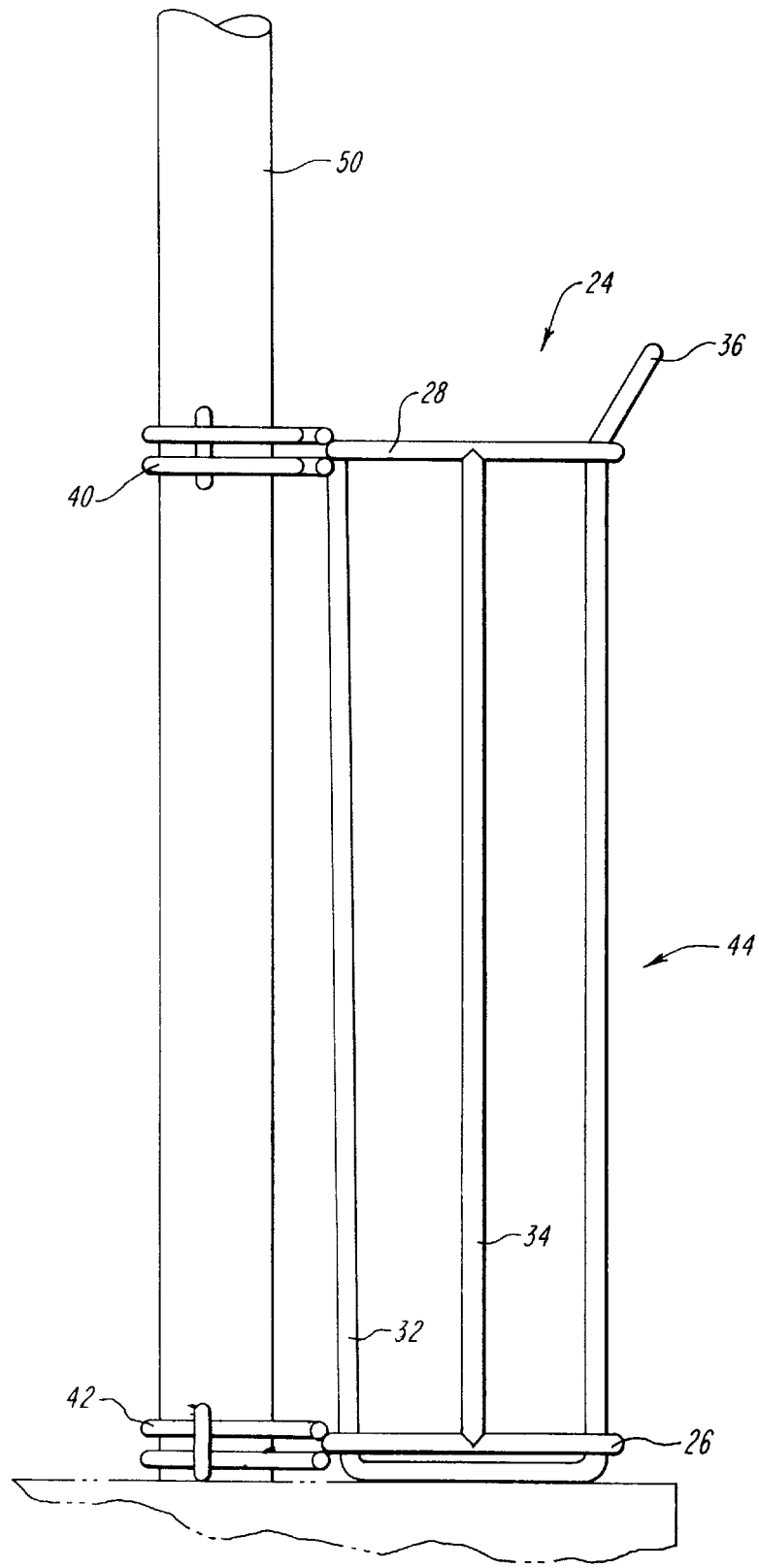
FIG. 3 is a side elevational view of the holder of FIG. 1, illustrating the holder mounted on a stand.

The holder 20 preferably includes a handle 36 coupled to the housing 24. The handle 36 is positioned to inhibit interference with positioning of the chest drain 22 within the housing 24. With reference to FIG. 3, the handle 36 is coupled to the housing 24 in selected proximity to the top member 28 and positioned at an angle to the plane of the top member 28 and to the plane of the front face 44 of the housing so that the handle does not interfere with positioning the chest drain 22 in the holder 20. One advantage of the handle 36 is that it allows the chest drain 22 to be easily carried by a patient or a medical professional. In addition, the above-described angled handle acts as a guide for the insertion of a chest drain.

Figure 6:
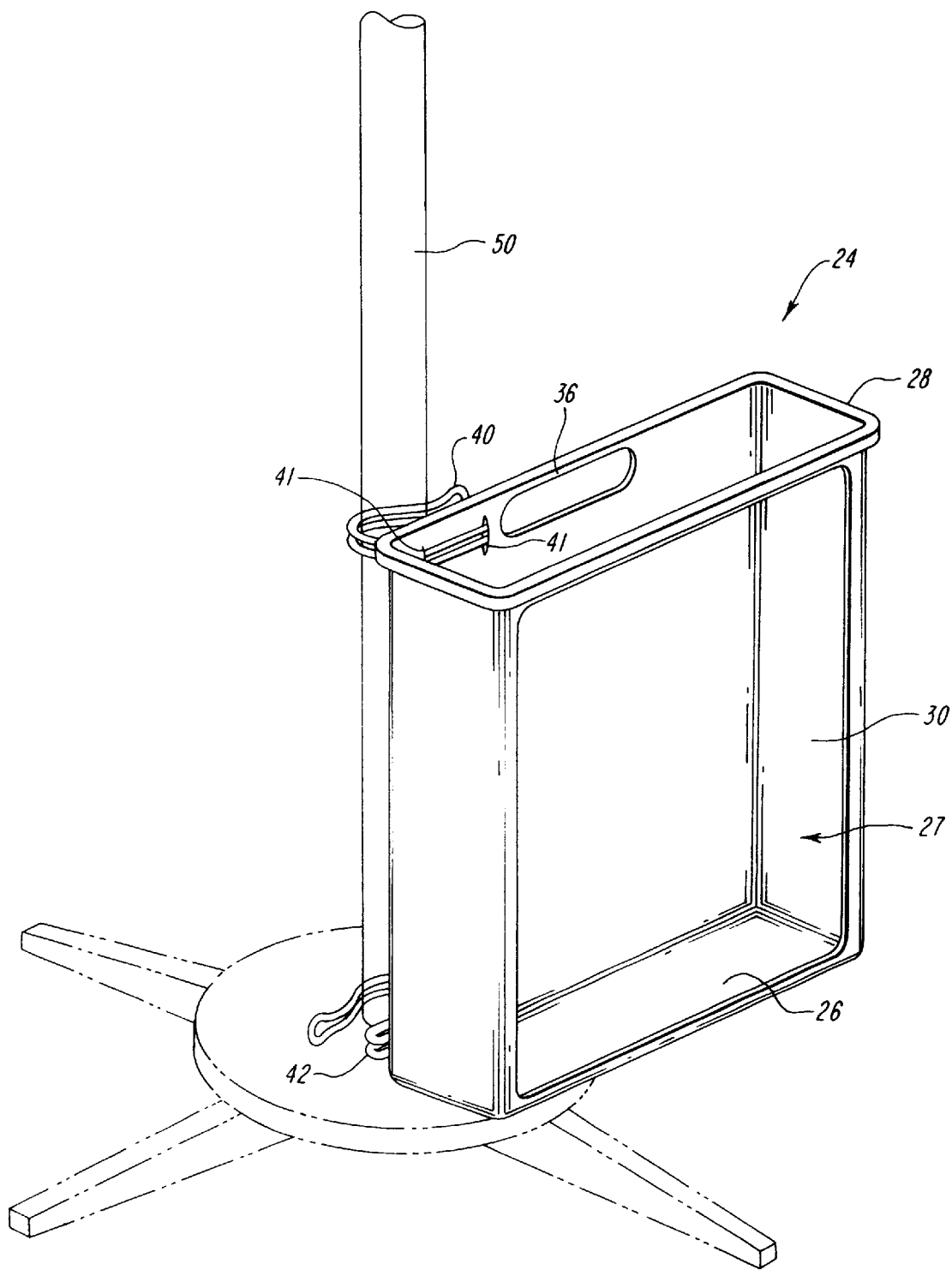
FIG. 6 is a perspective view of an alternative embodiment of a holder for mounting a chest drain on a support according to the teachings of the present invention.

An alternative version of the housing 24 is shown in FIG. 6. In this alternative version, the housing 24 has an opening 27 to facilitate inspection of the chest drain 22 when the chest drain 22 is positioned in the holder 20. The housing 24 has an integral handle 36, and slots 41 to accommodate hooks 40, 42. In another embodiment of the invention, the opening 27 can be filled instead with a transparent material. In fact, the entire housing 24 may be formed of a transparent material. The housing 24 is preferably made of a molded plastic.

With reference to FIGS. 1, and 4, the hooks 40, 42 preferably face in opposite directions. Furthermore, the common vertical axis 72 of the hooks 40, 42 are offset from the central vertical axis 74 of the back face 46 of the holder 20. In operation, as a result of this configuration of the hooks 40, 42, one can mount the holder 20 on a stand 50 and allow the holder to slide down the stand 50 until it rests on the base 66 of the stand, as can be seen in FIGS. 7A–7B.

This configuration of the hooks 40, 42 results in a holder 20 that is stable when mounted on a stand 50 even absent a clasp 62 for securing the hooks 40, 42 on the stand 50. More particularly, this configuration of the hooks 40, 42, on the holder 20, allows the weight of the holder 20 and of the chest drain to assist in keeping the hooks on the support 50. In other words, the moment arm of the holder and the chest drain acts to seat the hooks on the support 50. This configuration reduces the need for a tight fit between the hooks 40, 42 and the support 50. Alternatively, the hooks 40, 42 can be configured to tightly engage with the stand 50 by minimizing clearance between the hook 40 and the stand 50 such that, upon mounting the holder 20 on the stand 50, the holder 20 will not slide down the stand 50 to rest on the base 66. Subsequently, one can lower the fluid recovery device 22 into the holder, as shown in FIG. 7C.

More specifically and with reference to FIGS. 4, 5 and 7A–7C, when a user mounts a holder 20 on a support 50, the user places the holder at an angle to the support 50, with the openings of the hooks 40, 42 facing the support 50 and with the back face 46 adjacent to the support. Then, in order to mount the holder 20 on the support 50, the user rotates the holder 20, bringing the common vertical axis 72 of the hooks 40, 42 in alignment with the center of the support, and causing the support 50 to engage the hooks 40, 42. In one embodiment, the holder 20 is then supported by the hooks 40, 42 and the base 66 of the stand. Finally, as shown in FIG. 7C, the user can lower the fluid recovery device 22 into the holder.

Figure 8:
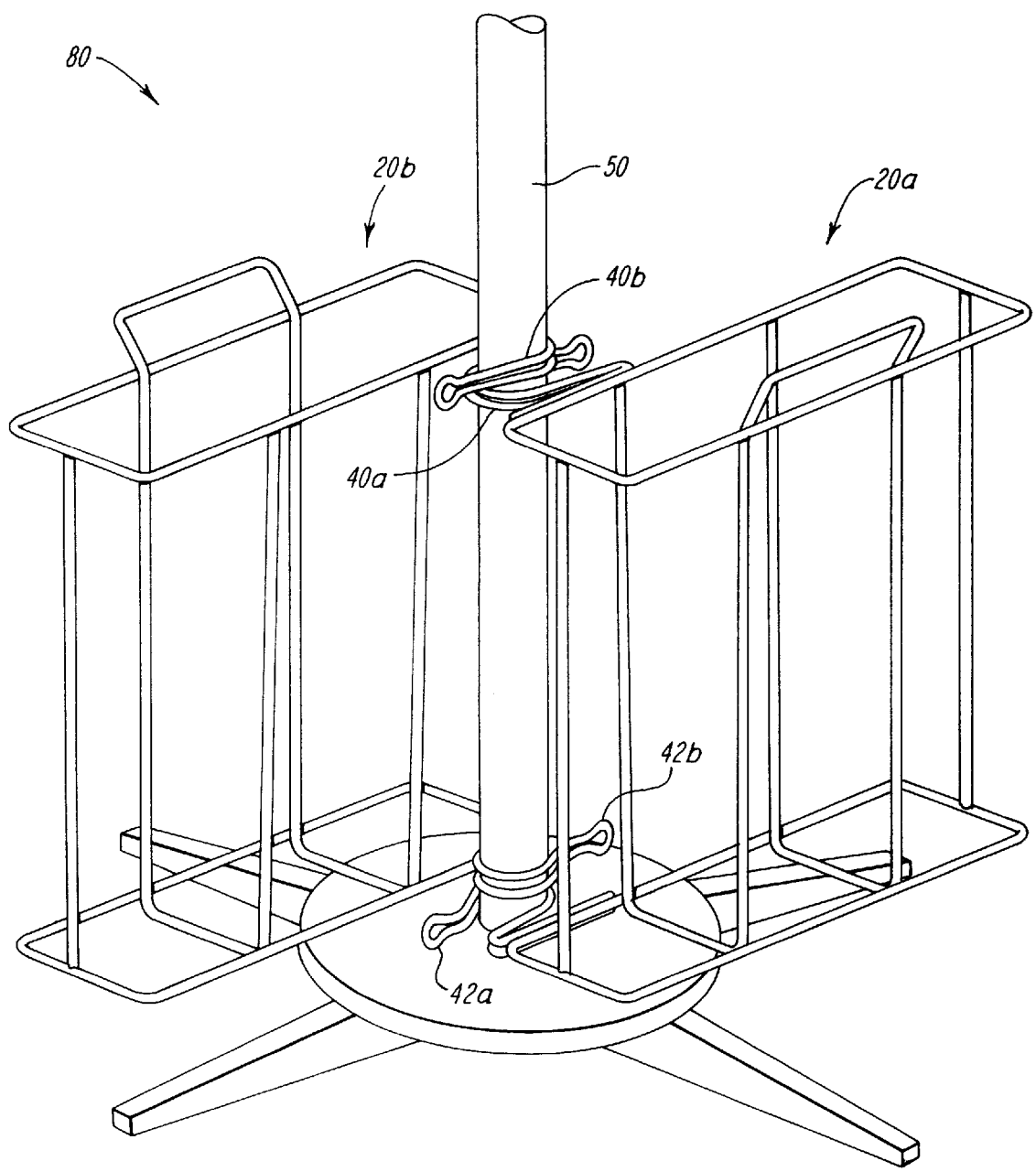
FIG. 8 is a perspective view of two holders according to FIG. 1 mounted on a single support.

A single patient can require more than one fluid recovery system. Alternatively, two patients with fluid recovery systems may need to share a single support 50. Thus, as shown in FIG. 8, the present invention provides chest drain support assembly 80 that permits two holders 20a, 20b to mount on a single support 50.

A user can mount a first holder 20a, and the holder 20a will rest on the support 50 supported by the base 66 and the two hooks 40a, 42a. A user can then mount a second holder 20b on the other side of the support, i.e., approximately 180° rotated about the common axis of the hooks 40a, 42a and the central axis of the support 50 from the first holder. The user raises the second holder 20b up about fifteen cm so that now the bottom hook 42b and the top hook 40b are just above the bottom and lower hooks 42a, 40a of the previously mounted holder 20a. The user can now mount the second holder 20b on the support 50 and the second holder 20b will slide down so that the hooks 40b, 42b of the second holder lie on top of the hooks 40a, 42a of the first holder 20a. The second holder will be sitting about 1 to 2 cm higher than the first holder 20a. Moreover, further holders may be mounted on the support 50 by using hooks that tightly engage the support 50 preventing the additional holders from sliding down onto holders 20a and 20b. Alternatively, three holders 20 can be mounted on the same horizontal level each holder rotated one hundred twenty degrees from the other holders.

Figure 10:
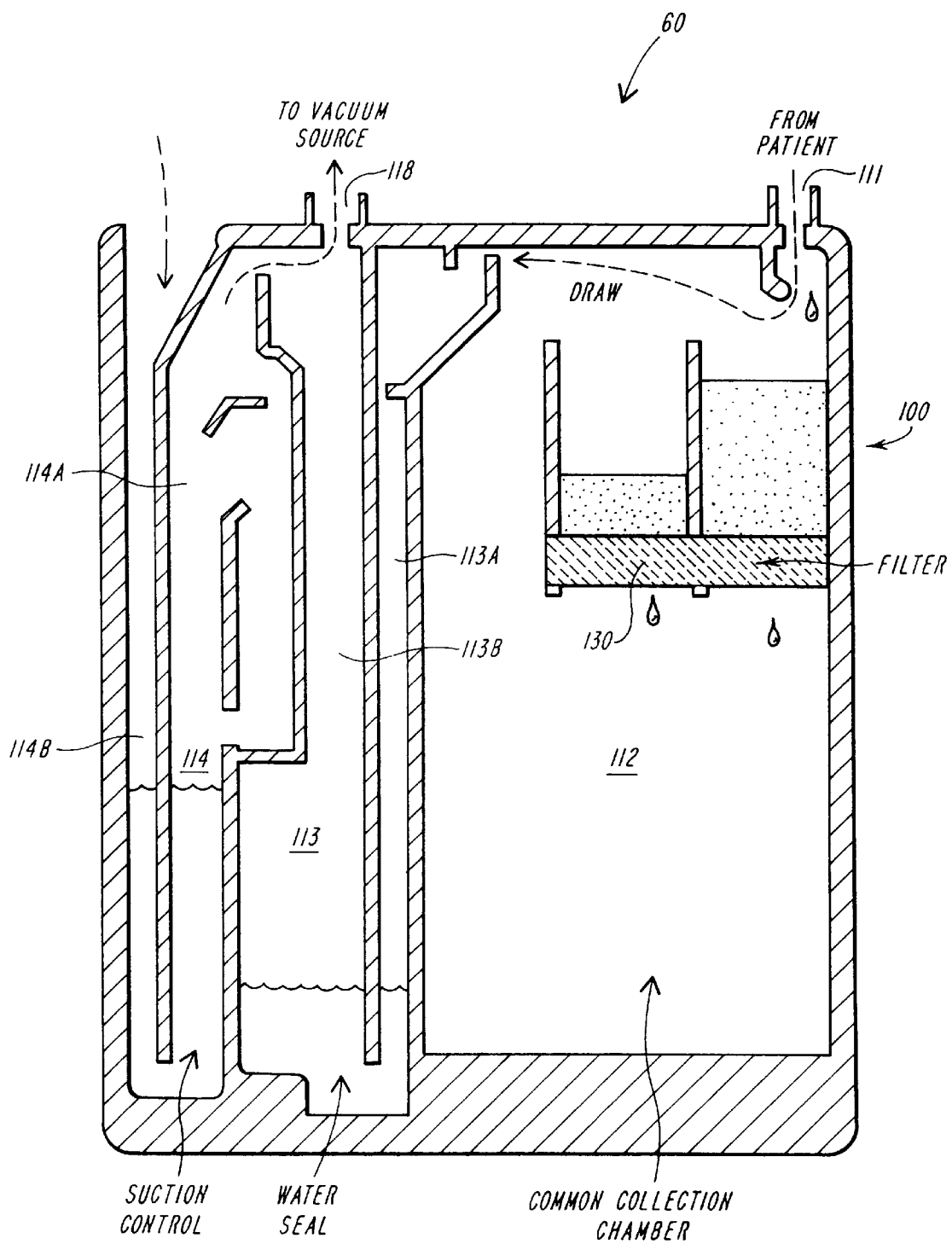
FIG. 10 is a front sectional view of an exemplary fluid recovery system that can be inserted into the holder of FIG. 1.

An exemplary thoracic cavity drain 60 is illustrated in FIG. 10. The thoracic cavity drain 60 generally includes a collection chamber 112, a U-shaped water seal chamber 113, and a suction control or manometer chamber 114. The structure and operation of the exemplary thoracic cavity drain 100 is described in detail in U.S. Pat. No. Re. 35,225, which is incorporated herein by reference. As shown in FIG. 10, blood and other fluids from a patient's body cavity enter the thoracic cavity drain 100 through an inlet port 111 and are collected in collection chamber 112 after passing through a gross filter 130 which traps macroscopic debris, such as blood clots, bone fragments and the like entrained in the incoming fluid. Water seal chamber 113 provides a barrier to reflux of atmospheric air into a patient's pleural cavity. Water seal chamber 113 is a U-shaped chamber having two arms 113A and 113B. Arm 113A is of smaller cross-sectional area than arm 113B and communicates with collection chamber 112. Arm 113b includes a vacuum port 118 for connection to an outside source of vacuum. Water seal chamber 113 communicates with arm 114A of manometer chamber 114. Arm 114B of the manometer chamber 114 is vented to the atmosphere. The manometer chamber 114 regulates vacuum by allowing air at atmospheric pressure to pass through the manometer water column into the water seal chamber 113. The amount of water in the manometer chamber 114 serves to regulate the sub-atmospheric pressure in chambers 112 and 113 generated by the vacuum source attached to port 118. The chest drain described above is exemplary. Other types of chest drains, such as dry chest drains employing a dry or non-fluid seal, can be used with the holder 20 of the present invention as well.

Figure 12:
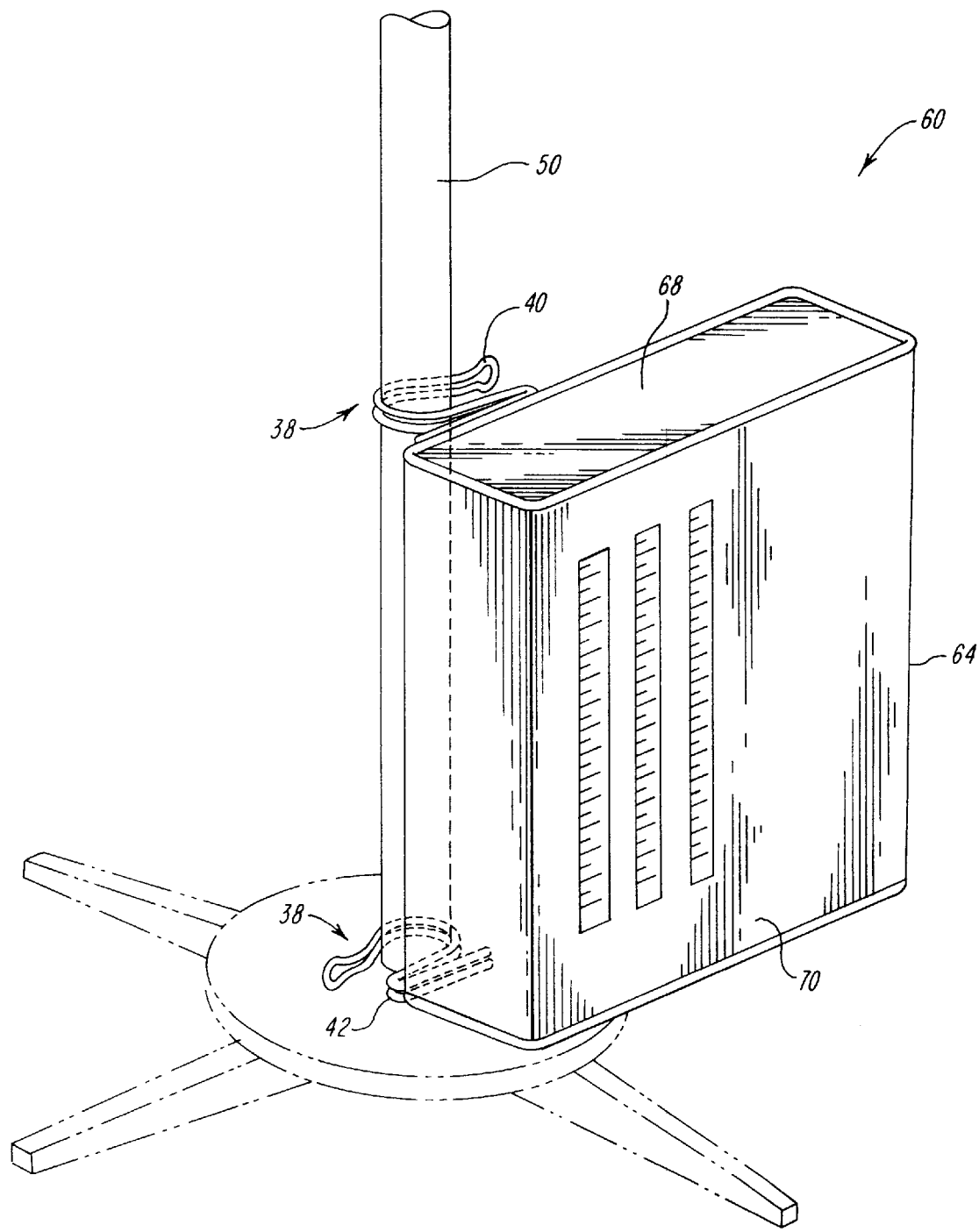
FIG. 12 is a perspective view of an alternative embodiment of the invention, illustrating a chest drain assembly mounted on a support.

With reference to FIG. 12, an alternative version of the invention provides a chest drain 60 suitable for mounting on a support 50. The chest drain 60 includes an external casing 64, and assembly 38 for mounting the casing 64 on the support 50. As illustrated, the assembly for mounting the casing includes first and second hooks 40, 42. In one embodiment, the first and second hooks 40, 42 are fixedly mounted in proximity to the top 68 of the casing and to the bottom 70 of the casing, respectively. In an alternative embodiment, the first and second hooks 40, 42 are removably and replaceably mounted to the casing 64. Those skilled in the art will appreciate that the mounting assembly is not limited to clamps or hooks.

Figure 13:
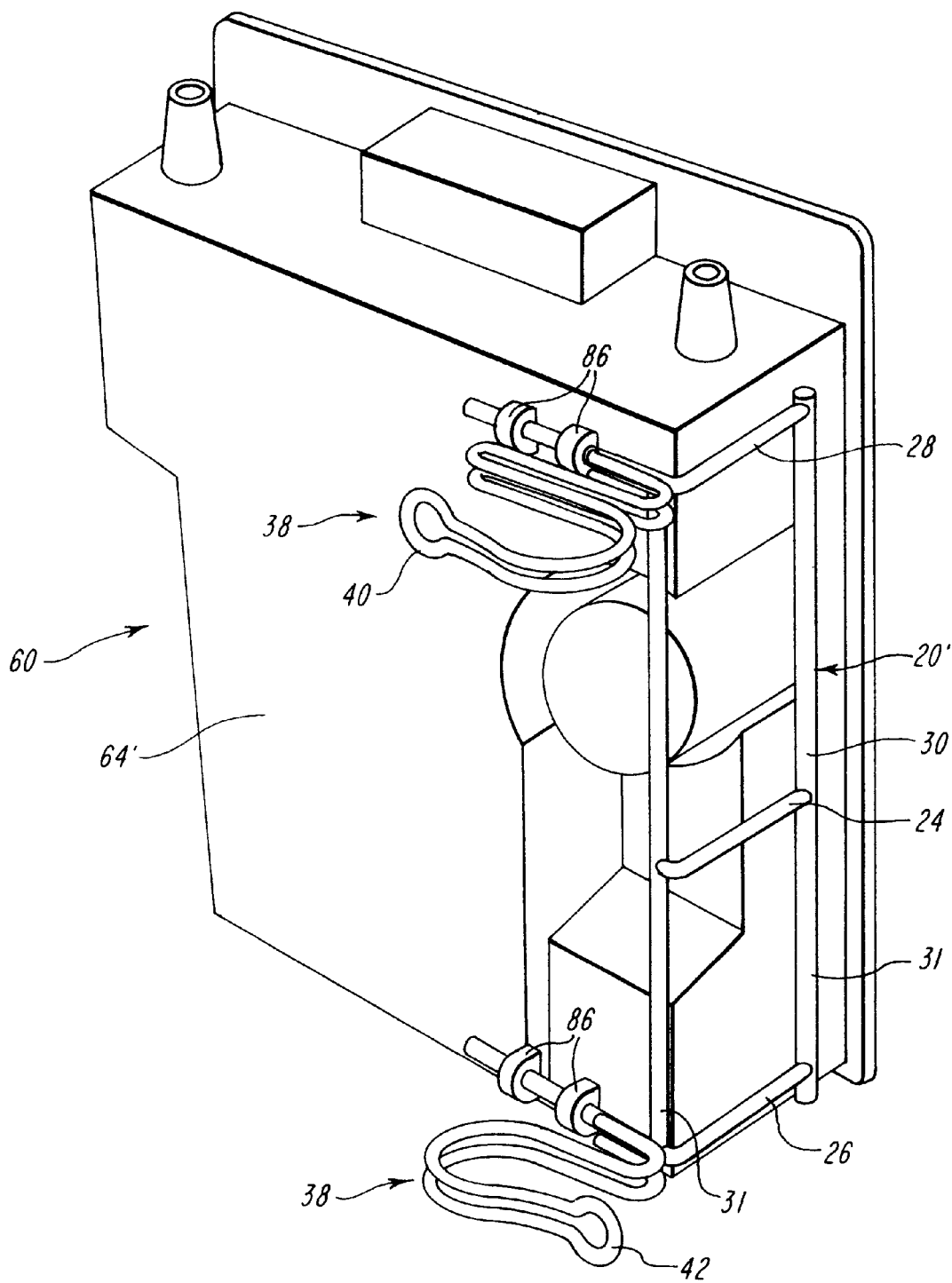
FIG. 13 is a perspective view of another alternative embodiment of the invention, illustrating a molded feature for mounting a chest drain holder to a chest drain.

With reference to FIG. 13, another alternative version of the invention provides a chest drain 60 suitable for mounting on a support. In the illustrated embodiment, the chest drain 60 includes first and second molded mating elements 86 for receiving a holder 20' having a housing 24. The mating elements 86 are integrally molded to the housing 64' of the chest drain 60. The first and second mating elements 86 are located in selected proximity to the top and to the bottom, respectively, of the chest drain 60. The mating elements 86 include at least one hole for receiving at least a portion of the housing 24 of the holder 20'.

The housing includes a top member 28, a base member 26, and a connecting assembly 30. In particular, the housing includes a generally L-shaped top member 28 and a generally L-shaped base member 26. The connecting assembly 30 includes two support members 31 which can be straight metal rods. In addition, the holder 20 includes a mounting assembly 38 for mounting the chest drain 60 on a support. In the illustrated embodiment, the mounting assembly 38 includes first and second hooks 40, 42. The holder 20 is replaceably and removably mounted on the chest drain 60.

The chest drain 60 is configured to receive the housing 24 of the holder 20. The chest drain is preferably configured to couple to the housing so that the housing does not extend beyond the widest dimension of the chest drain casing 64'. The chest drain 60 is configured to couple to the holder 20 so that the holder 20 can support the chest drain 60. One advantage of the holder 22 of the present invention is that one can mount the holder on a variety of supports, such as a free-standing support, e.g., an IV pole, as shown in FIG. 1, or a bedpost, as shown in FIG. 9 or can be carried by a patient without mounting. Another advantage of the holder 22 of the present invention is that one can mount multiple holders on a single support 50, as illustrated in FIG. 8.

Although the exemplary holder 20 has been described and illustrated as being a parallelepiped with a rectangular cross-section, one skilled in the art will recognize that the holder of the present invention is not limited to this geometry and can be configured in alternative shapes without departing from the scope of the invention. Additionally, one skilled in the art will recognize that the holder 20 is not limited to use with the exemplary thoracic cavity drain 60 described above, but can be effectively used with other types of thoracic cavity drains and other types of fluid recovery systems.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A holder for mounting a chest drain on a support, said holder comprising:
   a housing having an opening sized and shaped to receive the chest drain, and
   mounting means for removably and replaceably mounting said housing on the support, said mounting means being coupled to said housing.

2. A holder as recited in claim 1, wherein said mounting means comprises
   a hook coupled to said housing.

3. A holder as recited in claim 2, wherein said hook comprises
   a proximal fastening element for fastening said hook to said housing,
   a generally C-shaped element coupled to said fastening element and configured to conform to the support, and
   a spring-loaded distal element coupled to said C-shaped element and configured to extend and contract so as to allow said hook to receive the support.

4. A holder as recited in claim 2, wherein said mounting means further comprises
   hook securing means for securing said hook to said support.

5. A holder as recited in claim 4, wherein said hook securing means is a clasp.

6. A holder as recited in claim 1, wherein said housing comprises
   a base member,
   a top member opposed to said base member, said top member having said opening sized and shaped to receive the chest drain, and
   a connecting member for connecting said base member and said top member.

7. A holder as recited in claim 6, wherein said mounting means comprises
   first and second hooks coupled to said housing.

8. A holder as recited in claim 7, wherein said first and second hooks are coupled to said top member and bottom member, respectively.

9. A holder as recited in claim 8, wherein said first and second hooks are positioned to open in opposite directions.

10. A holder as recited in claim 1, further comprising
    a handle coupled to said housing.

11. A holder as recited in claim 10, wherein said handle is positioned to inhibit interference with positioning of the chest drain within said housing.

12. A holder as recited in claim 1, wherein at least a portion of said holder is made of stainless steel.

13. A holder as recited in claim 1, wherein said housing includes support members positioned to permit visual inspection of the chest drain when the chest drain is positioned in said housing.

14. A holder as recited in claim 1, wherein said housing is structured to permit visual inspection of the chest drain when the chest drain is positioned in said housing.

15. A holder for mounting a chest drain on a support, said holder comprising
    a frame for housing the chest drain, said frame comprising
      a base member,
      a top member opposed to said base member, said top member having an opening of a size and a shape to receive the chest drain,
      a connecting assembly for connecting said base member to said top member, and
      mounting means for removably and replaceably mounting said frame on said support.

16. A holder as recited in claim 15, wherein said mounting means comprises
    a hook coupled to said housing.

17. A holder as recited in claim 16, wherein said hook comprises
    a proximal fastening element for fastening said hook to said housing,
    a generally C-shaped element coupled to said fastening element and configured to conform to the support, and
    a spring-loaded distal element coupled to said C-shaped element and configured to extend and contract so as to allow said hook to receive said support.

18. A holder as recited in claim 16, wherein said mounting means further comprises
    hook securing means for securing said hook to said support.

19. A holder as recited in claim 18, wherein said hook securing means is a clasp.

20. A holder as recited in claim 15, wherein said mounting means comprises
    first and second hooks coupled to said housing.

21. A holder as recited in claim 20, wherein said first and second hooks are coupled to said top member and bottom member, respectively.

22. A holder as recited in claim 21, wherein said first and second hooks are positioned to open in opposite directions.

23. A holder as recited in claim 15, wherein said frame has a front face and an opposed back face and wherein said connecting member is configured to allow visual inspection of the chest drain through said front face and through said back face of said frame when the chest drain is positioned in said holder.

24. A holder as recited in claim 23, wherein said holder further comprises a handle coupled to said housing in selected proximity to said top member and positioned at an angle to said front face of said frame so that said handle does not interfere with insertion and removal of the chest drain from said holder.

25. A holder as recited in claim 15, wherein at least a portion of said holder is made of stainless steel.

26. A holder as recited in claim 15, wherein said connecting assembly comprises first and second U-shaped rods having an open portion and an opposed closed portion, each rod oriented substantially perpendicularly to said top member and to said bottom member, said top member being connected to said U-shaped rods in selected proximity to the open portion of said U-shaped rods, and said bottom member being connected to said U-shaped rods in selected proximity to the closed portion of said U-shaped rods.

27. A holder as recited in claim 15, wherein said connecting assembly comprises a U-shaped rod having an open portion and an opposed closed portion, said rod oriented substantially perpendicularly to said top member and to said bottom member, said top member being connected to said U-shaped rod in selected proximity to the open portion of said U-shaped rod, and said bottom member being connected to said U-shaped rod in selected proximity to the closed portion of said U-shaped rod.

28. A holder for housing a chest drain, said holder comprising a frame for housing the chest drainage device, said frame having a base member and having an opening opposed to said base member, said opening being of a shape and size to receive the chest drain.

29. A holder as recited in claim 28, wherein said holder further comprises mounting means for removably and replaceably mounting said housing on said support, said mounting means being coupled to said housing.

30. A holder as recited in claim 29, wherein said mounting means comprises a hook coupled to said housing.

31. A holder as recited in claim 30, wherein said hook comprises a proximal fastening element for fastening said hook to said housing, a generally C-shaped element coupled to said fastening element and configured to conform to the support, and a spring-loaded distal element coupled to said C-shaped element and configured to extend and contract so as to allow said hook to receive said support.

32. A holder as recited in claim 30, wherein said mounting means further comprises hook securing means for securing said hook to said support.

33. A holder as recited in claim 32, wherein said hook securing means is a clasp.

34. A holder as recited in claim 29, wherein said frame comprises a base member, a top member opposed to said base member, said top member having an opening of a size and shape to receive the chest drain, a connecting member for connecting said base member and said top member.

35. A holder as recited in claim 34, wherein said mounting means comprises first and second hooks coupled to said frame.

36. A holder as recited in claim 35, wherein said first and second hooks are coupled to said top member and bottom member, respectively.

37. A holder as recited in claim 36, wherein said first and second hooks are positioned to open in opposite directions.

38. A holder as recited in claim 29, further comprising a handle coupled to said frame.

39. A holder as recited in claim 38 wherein said handle is positioned to inhibit interference with positioning of the chest drain within said frame.

40. A holder as recited in claim 29, wherein at least a portion of said holder is made of stainless steel.

41. A holder as recited in claim 29, wherein said frame includes support members positioned to permit visual inspection of the chest drain when the chest drain is positioned in said housing.

42. A holder as recited in claim 29, wherein said frame is structured to permit visual inspection of the chest drain when the chest drain is positioned in said housing.

43. A holder for mounting a chest drain on a support, said holder comprising a housing for carrying the chest drain, said housing having an opening sized and shaped to receive the chest drain, and a mounting element coupled to said housing, said mounting element removably and replaceably mounting said housing on said support.

44. A holder as recited in claim 43, wherein said mounting element comprises first and second hooks coupled to said housing.

45. A holder as recited in claim 44, wherein said first and second hooks are positioned to open in opposite directions.

46. A holder as recited in claim 45, wherein said holder has a back face with a central axis, and wherein said first and second hooks have a common axis offset from said central axis of said back face.

47. A holder as recited in claim 43, further comprising a handle coupled to said housing, said handle being configured to inhibit interference with positioning of the chest drain within said housing.

* * * * *